US010265717B2

(12) United States Patent
Erdmann et al.

(10) Patent No.: US 10,265,717 B2
(45) Date of Patent: Apr. 23, 2019

(54) METHOD OF CONTROLLING THE SPRAY DROPLET SIZE OF A SPRAY NOZZLE APPARATUS FOR SPRAY-DRYING APPLICATIONS, SPRAY DRYING APPARATUS AND NOZZLE THEREFORE

(71) Applicant: NESTEC S.A., Vevey (CH)

(72) Inventors: Peter Erdmann, Bern (CH); Peter Frankhauser, Konolfingen (CH); Martin Nydegger, Konolfingen (CH); Dale Richard Sanders, Courgevaux (CH); Christian Schmied; Michael Stranzinger, Munsingen (CH); Gerhard Walthert, Aeschlen (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 15/540,454
(22) PCT Filed: Dec. 22, 2015
(86) PCT No.: PCT/EP2015/081013
§ 371 (c)(1),
(2) Date: Jun. 28, 2017
(87) PCT Pub. No.: WO2016/107795
PCT Pub. Date: Jul. 7, 2016

(65) Prior Publication Data
US 2018/0001334 A1 Jan. 4, 2018

(30) Foreign Application Priority Data
Dec. 31, 2014 (EP) .................................. 14200753

(51) Int. Cl.
B05B 12/08 (2006.01)
A23C 1/04 (2006.01)
(Continued)

(52) U.S. Cl.
CPC ............. *B05B 12/085* (2013.01); *A23C 1/04* (2013.01); *A23L 3/46* (2013.01); *A23P 10/40* (2016.08);
(Continued)

(58) Field of Classification Search
CPC ... B05B 12/085; B05B 1/3447; B05B 1/3013; F26B 3/12; A23P 10/40; B01J 2/04; A23C 1/04; A23L 3/46; B01D 1/18; G01N 11/00
(Continued)

(56) References Cited

U.S. PATENT DOCUMENTS 3,981,957 A 9/1976 Van Brederode et al.
6,558,127 B2 * 5/2003 Maruyama ................ F04B 7/06
222/333

(Continued)

FOREIGN PATENT DOCUMENTS

CN 101542405 9/2009
DE 935495 11/1955
(Continued)

OTHER PUBLICATIONS

Written Opinion of the International Searching Authority for International Application No. PCT/EP015/081013 dated Jul. 3, 2016.
(Continued)

*Primary Examiner* — Arthur O. Hall
*Assistant Examiner* — Steven M Cernoch
(74) *Attorney, Agent, or Firm* — K&L Gates LLP

(57) ABSTRACT

A method of controlling the spray droplet size of a spray nozzle apparatus, in particular for the manufacturing of food powders, delivered to the spray nozzle comprises the following steps: a) providing a paste of a product to be sprayed by a spray nozzle; b) continuously determining the shear viscosity ($\eta$) of the product paste delivered to the spray nozzle; c) determining the mass flow rate (Qrn) of the product paste delivered to the spray nozzle; d) determining the static pressure (P) of the product paste delivered to the spray nozzle; e) determining the density ($\rho$) of the product paste delivered to the spray nozzle; f) delivering the data
(Continued)

obtained in steps b) to e) to a control device comprising a computer and a memory; g) calculating control data for adjusting the spray nozzle on the basis of the data obtained in steps b) to e) and on nozzle geometry parameters stored in the memory; h) sending the control data as control signals to a control means of the spray nozzle and adjusting the spray nozzle accordingly.

15 Claims, 7 Drawing Sheets

(51) Int. Cl.
| | |
|---|---|
| A23L 3/46 | (2006.01) |
| B01D 1/18 | (2006.01) |
| F26B 3/12 | (2006.01) |
| A23P 10/40 | (2016.01) |
| B05B 1/34 | (2006.01) |
| B01J 2/04 | (2006.01) |
| B05B 1/30 | (2006.01) |
| G01N 11/00 | (2006.01) |

(52) U.S. Cl.
CPC ............... *B01D 1/18* (2013.01); *B01J 2/04* (2013.01); *B05B 1/3013* (2013.01); *B05B 1/3447* (2013.01); *F26B 3/12* (2013.01); *A23V 2002/00* (2013.01); *G01N 11/00* (2013.01)

(58) Field of Classification Search
USPC ........ 251/264, 273, 274, 275, 276, 277, 278
See application file for complete search history.

(56) References Cited

U.S. PATENT DOCUMENTS

| | | | | |
|---|---|---|---|---|
| 6,880,350 | B2* | 4/2005 | Tilton | G01R 31/2874 239/444 |
| 7,647,883 | B2* | 1/2010 | Maruyama | B05C 5/02 118/300 |
| 7,980,483 | B2* | 7/2011 | Stretch | F01M 13/04 239/1 |
| 8,689,459 | B2* | 4/2014 | Poortinga | B01J 2/18 239/596 |
| 8,978,364 | B2* | 3/2015 | Olivier | F01N 3/2066 239/124 |
| 2003/0215515 | A1 | 11/2003 | Truong-Le et al. | |
| 2004/0118865 | A1* | 6/2004 | Maruyama | B05C 5/0225 222/1 |
| 2004/0227016 | A1* | 11/2004 | Yagi | B05B 1/265 239/524 |
| 2004/0228970 | A1* | 11/2004 | Maruyama | F04B 13/00 427/256 |
| 2006/0226265 | A1* | 10/2006 | Miller | B01J 4/002 239/585.1 |
| 2011/0052786 | A1 | 3/2011 | Poortinga et al. | |
| 2011/0253809 | A1* | 10/2011 | Bamber | B05B 1/3053 239/518 |
| 2013/0277453 | A1* | 10/2013 | Kobayashi | F02M 61/163 239/142 |
| 2013/0292498 | A1* | 11/2013 | Olivier | F01N 3/2066 239/585.1 |
| 2013/0327851 | A1* | 12/2013 | Kobayashi | F02M 61/162 239/489 |
| 2014/0070030 | A1* | 3/2014 | Harms | B05B 11/0067 239/583 |
| 2014/0106051 | A1 | 4/2014 | Lefevre et al. | |
| 2014/0346698 | A1 | 11/2014 | Rijfers et al. | |

FOREIGN PATENT DOCUMENTS

| | | |
|---|---|---|
| DE | 19617685 | 6/2017 |
| WO | 9748496 | 12/1997 |

OTHER PUBLICATIONS

Chinese Office Action in corresponding application No. 201580068387.7, dated Feb. 12, 2018, 10 pages.

* cited by examiner

METHOD OF CONTROLLING THE SPRAY DROPLET SIZE OF A SPRAY NOZZLE APPARATUS FOR SPRAY-DRYING APPLICATIONS, SPRAY DRYING APPARATUS AND NOZZLE THEREFORE

CROSS REFERENCE TO RELATED APPLICATIONS

The present application is a National Stage of International Application No. PCT/EP2015/081013, filed on Dec. 22, 2015, which claims priority to European Patent Application No. 14200753.3, filed on Dec. 31, 2014, the entire contents of which are being incorporated herein by reference.

The present invention is directed to a method of controlling the spray droplet size of a spray nozzle apparatus. It is further directed to a spray drying apparatus and a nozzle for such a spray drying apparatus.

The manufacturing of food powders is realized to a great extent by means of spray drying. This process converts emulsions, suspensions and dispersions into powder. Spray nozzles create droplets, which are dried in hot air by evaporating water. The final powder quality, the final powder texture, the dryer process design, the drying efficiency, the walls fouling behaviour, the operational safety, to name only a few characteristics, are directly linked to the spray quality and thus the atomization process.

Known spray drying processes use atomization nozzles with fixed geometries which cannot be adjusted inline to the process and product conditions during start-up, manufacturing operation and shut-down. Instead operators change the nozzle geometries prior to the production cycle without the possibility to cover all the manufacturing situations. Such nozzles are chosen according to water tables. The manufacturing of food powders happens at significantly higher viscosities compared to water. Typical spray viscosities are within in a range comprised between 1 to 300 mPas. There is no known nozzle apparatus capable to compete with such a wide range.

As an example, for dairy emulsions at concentrate total solids above 50%, the concentrate viscosity increases in an exponential slope with further increase of total solids. This fact causes problems to spray-drying, if the concentrate viscosity exceeds a design limit of the atomizer nozzles. The design limit is described by means of an atomizer air-core break-down, which stops the creation of droplets and thus stops efficient spray-drying and agglomeration of powders with a required texture. Using prior art spray nozzle apparatus, air-core break downs within atomizer nozzles cannot be determined visually, thus there is currently no means to operate the spray-drying process at its best point without facing issues, such as powder blockages in cones and cyclones, wall fouling or atomizer beard formation, to name just a few issues.

Since the product and process conditions change from start-up to shut-down of the process the quality of the product achieved varies and product buildup can happen on the nozzle itself and on the walls of the spray-drying equipment, in particular on the walls of the drying chamber, in cones of spray-dryers and cyclones, but also in the conveying ducts between the process units.

It is a first objective of the present invention to overcome the problems identified with prior art equipment and methods and to enable to operate a spray-drying equipment at its best point and in the most economical way, which involves to be able to spray material having the highest possible total solids content and dry to obtain a dry powder having the maximum total solid content possible, without exceeding the design limit of the atomizers nozzles, which is triggered by the air-core break-down.

It is an object of the present invention to obtain a method of controlling the spray droplet size of a spray nozzle apparatus which allows controlling of the spray droplet size during the working process. This is particularly useful to have achieve a target spray droplet size distribution defined by the Sauter diameter and to keep a target droplet size distribution constant even with changing product or material properties and changing process conditions.

This object is achieved by a method comprising the following steps:

a) providing a paste of a product to be sprayed by a spray nozzle;

b) continuously determining the shear viscosity ($\eta$) of the product paste delivered to the spray nozzle;

c) determining the mass flow rate (Qm) of the product paste delivered to the spray nozzle;

d) determining the spray pressure (P) of the product paste delivered to the spray nozzle;

e) determining the density ($\rho$) of the product paste delivered to the spray nozzle;

f) delivering the data obtained in steps b) to e) to a control device comprising a computer and a memory;

g) calculating control data for adjusting the spray nozzle on the basis of the data obtained in steps b) to e) and on nozzle geometry parameters stored in the memory;

h) sending the control data as control signals to a control means of the spray nozzle and adjusting the spray nozzle accordingly.

The shear viscosity is used as input parameter to control the spray nozzle. It allows inline control of the spray nozzle and thus of the spray droplet size, via a stability criterion composed of the spray mass flow rate Qm, the spray pressure P the product density ($\rho$) and the product viscosity ($\eta$).

This stability criterion ensures to operate the spray-nozzle within design limits, avoiding air-core break-downs in the swirl-chamber of the nozzle.

Furthermore, a consistent powder agglomeration is achieved in the product during a production cycle independent of the total amount of solid particles (TS) or independent of mass flow rate fluctuations. By this method, a process automation can be achieved through improved and simplified reproducibility and reliability of product properties for different spray-dryer types. A competitive production control is achieved by the inventive method via advanced design of final powder properties like powder moisture, tap density, final agglomerate size and agglomerate stability. Due to the automation the production economy and process efficiency (best-point operation) is also enhanced.

In a preferred embodiment step b) of continuously determining the shear viscosity ($\eta$) of the product paste delivered to the spray nozzle is carried out in a bypass to the product paste stream to the spray nozzle. The bypass has the advantage to measure the shear viscosity independent of the production mass flow rate to suit laminar flow conditions (at Reynolds Re<2300), which allows the measurement of the shear viscosity according to the Differential Pressure Drop Method.

Preferably, the shear viscosity ($\eta$) of the product paste is determined by the following steps:

b1) providing a constant feed-flow-rate of the product paste at laminar flow conditions;

b2) determining the mass flow of the product paste;

b3) delivering the product paste to a pressure-drop-meter and determining the pressure drop;

b4) calculating the shear viscosity ($\eta$) of the product paste on the basis of the laminar mass flow determined in step b2), the pressure drop determined in step b3) and a known product density.

In case the step b) is carried out in a bypass the calculation in step b4) considers also the bypass-mass-flow-rate.

Preferably, the determination of the pressure drop in step b3) is carried out according to the differential pressure drop method.

This method enables inline recording of product shear viscosities e. g. of coffee and milk products before atomization with its specific product characteristics such as highly viscous (1-300 mPas) and shear-thinning flow behaviour (determination of $2^{nd}$ Newtonian plateau viscosity ($\eta$). The inline shear viscosity information is necessary to operate the controllable spray-nozzle inline in order to determine the best point configuration of the atomizer and warn in case of design limit achieved. Thus, the inline differential pressure drop method allows a calibration of the shear viscosity for Newtonian and in particular Non-Newtonian shear-thinning fluids based on laboratory rheometers.

Other techniques to measure the shear viscosity are either underestimating or overestimating the predefined product shear viscosities of dairy and nutrition products (via laboratory rheometer). In particular for shear-thinning fluids, the frequency-based measuring technique, the Coriolis forced measuring method and the quartz-viscosimetry method do not give the possibility to determine the 2nd Newtonian plateau viscosity of shear-thinning fluids due to the lack of information concerning the applied flow field of the method (and thus unknown shear rates).

Thus, inline recording of the so called second Newtonian plateau viscosity of Non-Newtonian food fluids is possible with the differential pressure drop method and thus allows calibration with predefined product shear viscosity rheograms, which are found from laboratory rheometer measurements.

According to a second aspect of the invention the object concerning the spray drying apparatus is achieved by the features of claim 7.

The spray drying apparatus according to the invention provides an inline working means to control spray droplet sizes during spray drying. The spray quality can be judged in terms of the droplet size distribution and its corresponding droplet size mean diameter, i.e. the Sauter diameter $D_{32}$.

The spray drying according to the invention helps to achieve the following main manufacturing objectives: a minimum Sauter diameter for fastest and equilibrium water evaporation, an optimum powder agglomeration for consistent powder quality, an equilibrium powder particle size distribution for consistent powder quality, the elimination of scorched particles for consistent powder quality, minimal powder wall fouling and as a consequence reduced risk for cone, duct or conveying pipe powder blockages, minimal spray nozzle fouling and increased dryer safety because of the elimination of dripping and elimination of scorched particles.

According to a third aspect of the invention a spray nozzle apparatus is provided which comprises means for adjusting the nozzle chamber geometry based on spray drying process parameters, like spray mass flow rate, spray pressure and product parameters, like product density, product shear viscosity which parameters are obtained or evaluated inline during the spray drying process in accordance with a method of the present invention.

Thus it is possible to adjust the nozzle geometry inline on the basis of parameters responsible for the process yield and the quality of the product achieved. Furthermore the downtimes of a spray drying apparatus equipped with a spray nozzle apparatus according to the invention can be reduced since cleaning times are cut significantly thanks to minimised equipment fouling.

The nozzle apparatus can be provided with an electric drive adjusting the chamber geometry, the drive being controlled by a control device on the basis of spray drying process parameters and product parameters as mentioned above.

To modify the chamber geometry, according to an advantageous embodiment of the invention, the apparatus comprises a plunger for adjusting the volume of the nozzle swirl-chamber.

By moving the plunger into and out of the nozzle chamber by the electric drive an adjustment of the height of the nozzle swirl-chamber is achieved. Thus by moving the plunger, the geometry of the nozzle chamber can be modified inline during the manufacturing process in relation to the product and process parameters as mentioned above.

Movement of the plunger is achieved by the electric drive which in turn is controlled by a control device like a programmable circuit. This circuit transmits control signals to the electric drive as a function of the above-mentioned parameters.

In order to achieve the above, according to an advantageous embodiment of the invention the electric drive comprises an electric motor rotatably driving an output shaft, the rotation being transformed in to a longitudinal motion of the plunger via a threaded engagement between the output shaft and the plunger. Thus a mechanical stable and easy to handle configuration is achieved.

According to an embodiment of the invention, a connecting sleeve is provided which is releasably fixed to the electric drive and is equipped with a longitudinal bore for rotatably accommodating a hollow shaft which transfers the rotating motion of an output shaft of the electric drive to an adjusting pin driving the plunger axially into and out of the nozzle chamber.

The adjusting pin is provided with a longitudinally extending bore with an inner thread in engagement with an outer thread of the plunger such that a rotating motion of the adjusting pin is transformed into a longitudinal motion of the axially movable plunger.

According to an advantageous embodiment of the invention, the nozzle chamber is defined by a swirl chamber body being inserted into an inner chamber of a nozzle body, the nozzle body being releasably fixed to the connecting sleeve mentioned above and the swirl chamber body is provided with an opening channel which is arranged in correspondence to the orifice for entering the product material into the swirl chamber of the swirl chamber body. This material can for example be a paste for the production of dairy and nutrition products.

The swirl chamber can be provided with a helicoidally tightening guiding face for accelerating the paste into the direction of the nozzle orifice to output the material droplets with high speed. Since the material is incompressible, the cone angle of the spray cone and the droplet diameter can be modified according to the product and process parameters inline during the manufacturing process of the product to be achieved by the adjustable movement of the plunger within the swirl chamber.

According to an advantageous embodiment of the invention, the orifice for introducing the material into the nozzle chamber extends radially to the longitudinal axis of the nozzle and the product material is being transferred to the nozzle via a tube being connected to the orifice.

To enable a basic modification of the output characteristics of the spray nozzle, the nozzle body is equipped with a releasably mounted orifice plate such that the opening diameter of the nozzle orifice is variable by replacing the orifice plate by a different diameter orifice plate.

According to a preferred characteristic, a cone angle of a spray mist produced by product droplets and the droplet size are variable by axially moving the plunger relative to the nozzle chamber.

In the following the invention will be described in further detail by means of an embodiment thereof and the appended drawings.

Figure 1:
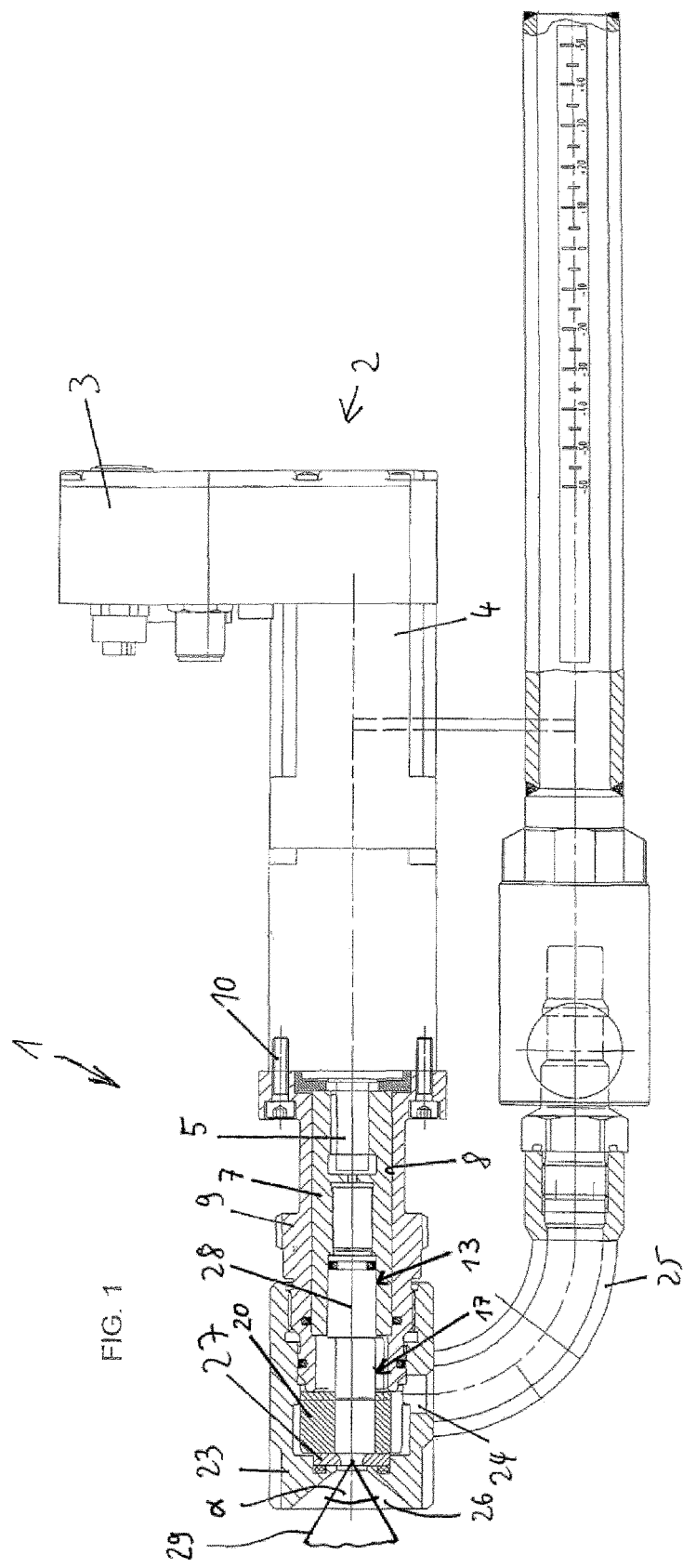
FIG. 1 shows a partial sectional side view of an embodiment of a spray nozzle apparatus according to the invention.

The spray nozzle apparatus 1 according to FIG. 1 comprises an electric drive 2 provided with an interface (such as a Profibus interface) and a power supply (such as a 24V-DC power supply) at 3 and an electric motor 4 including a transmission connected with 3.

Figure 2:
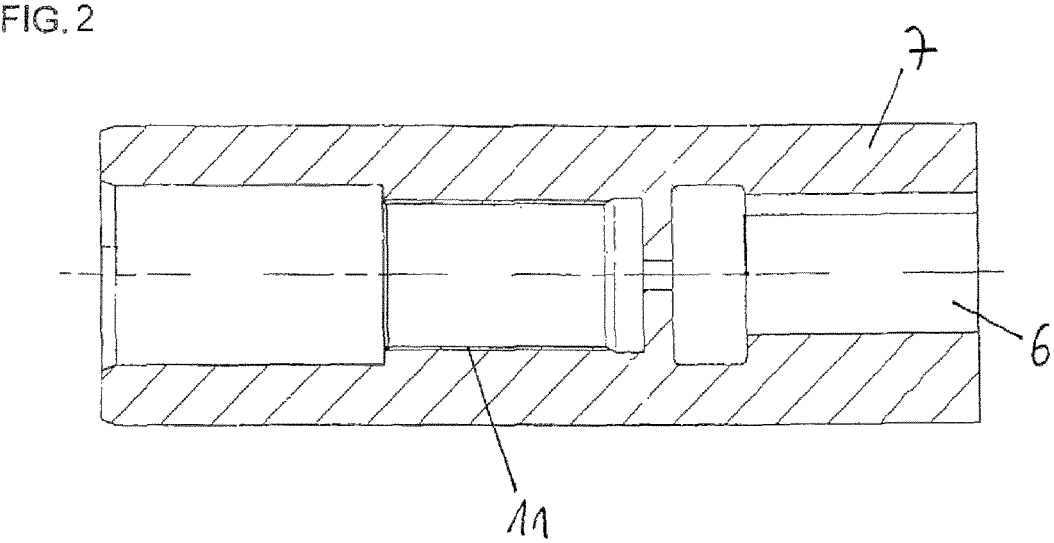
FIG. 2 shows a cross sectional view of a hollow shaft of the spray nozzle apparatus of FIG. 1.

The electric motor 4 drives an output shaft 5 in a rotating manner. The output shaft 5 extends into a longitudinally extending inner bore 6 of a hollow shaft 7 which is depicted in more detail in FIG. 2.

The hollow shaft 7 is rotatably accommodated in a longitudinally extending inner bore 8 of a connecting sleeve 9 which can be fixed to the housing of transmission 4 by bolts 10.

Figure 3:
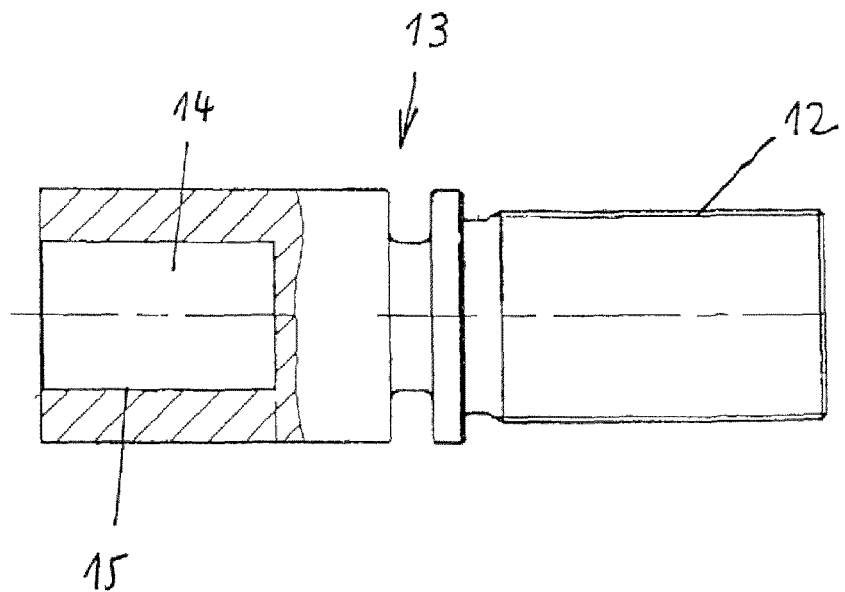
FIG. 3 shows a partial sectional view of an adjusting pin.

The inner bore 6 of the hollow shaft 7 is equipped with an inner thread 11 which can be brought into a threaded engagement with an outer thread 12 provided on an end piece of an adjusting pin 13—shown in more detail in FIG. 3—which can be inserted into the inner bore 6 of the hollow shaft 7.

Opposite to the threaded terminal end 12 of the adjusting pin 13 there is provided a receiving section of the adjusting pin 13, which is formed with an inner bore 14 equipped with an inner thread 15.

Figure 5:
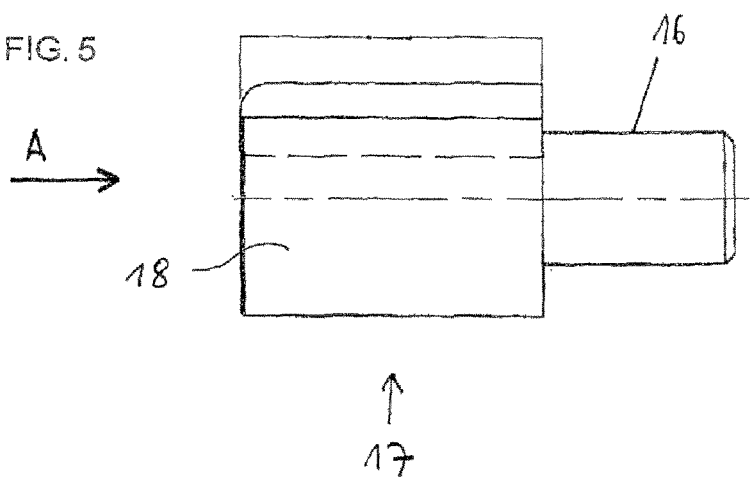
FIGS. 5 and 5A depict a side view and a front view (in the direction of arrow A) of the plunger of the spray nozzle apparatus of FIG. 1.
Figure 5A:
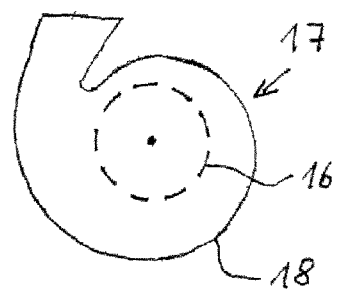
Figure 6:
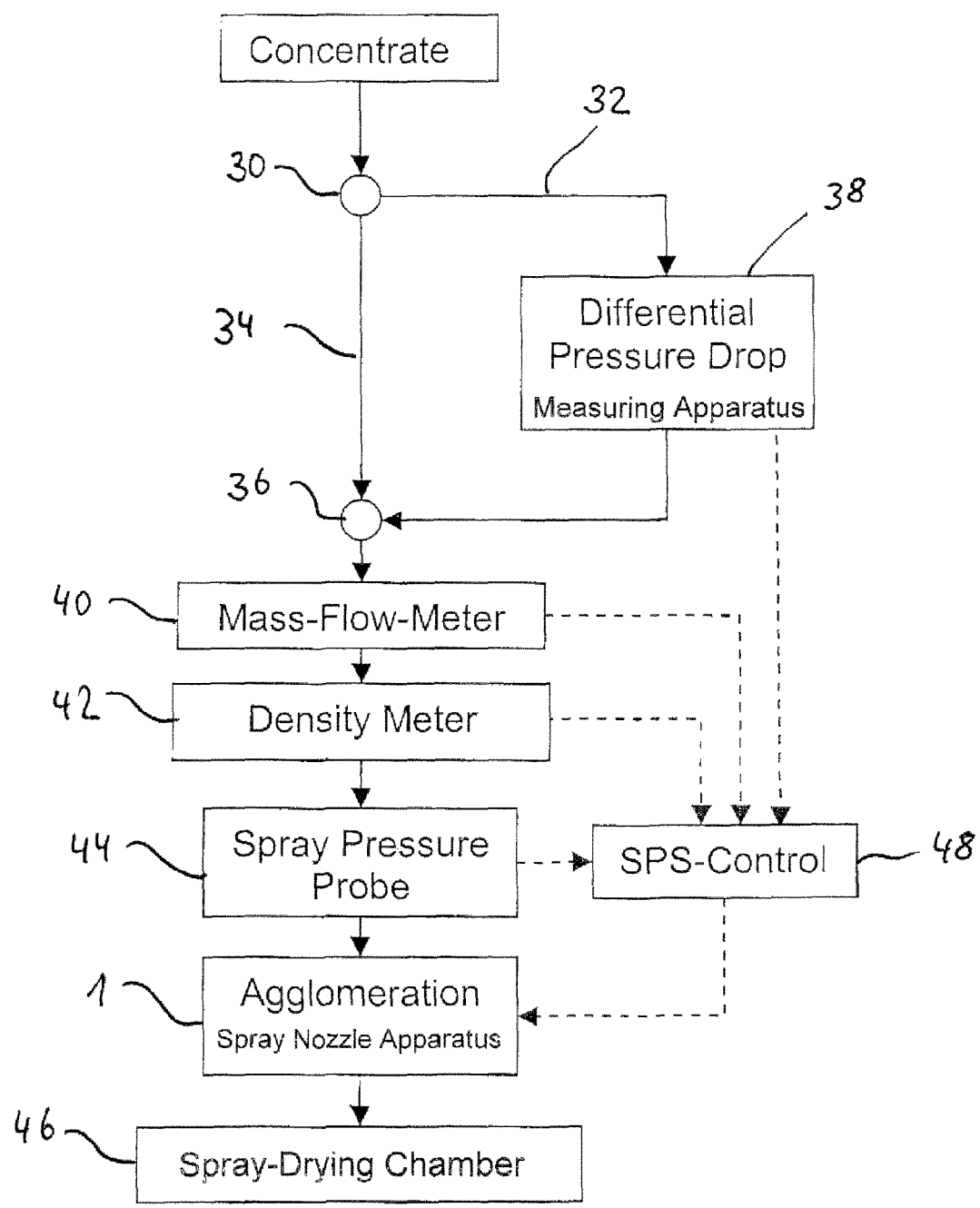
FIG. 6 is a flow chart of the process control method according to the invention.
Figure 7:
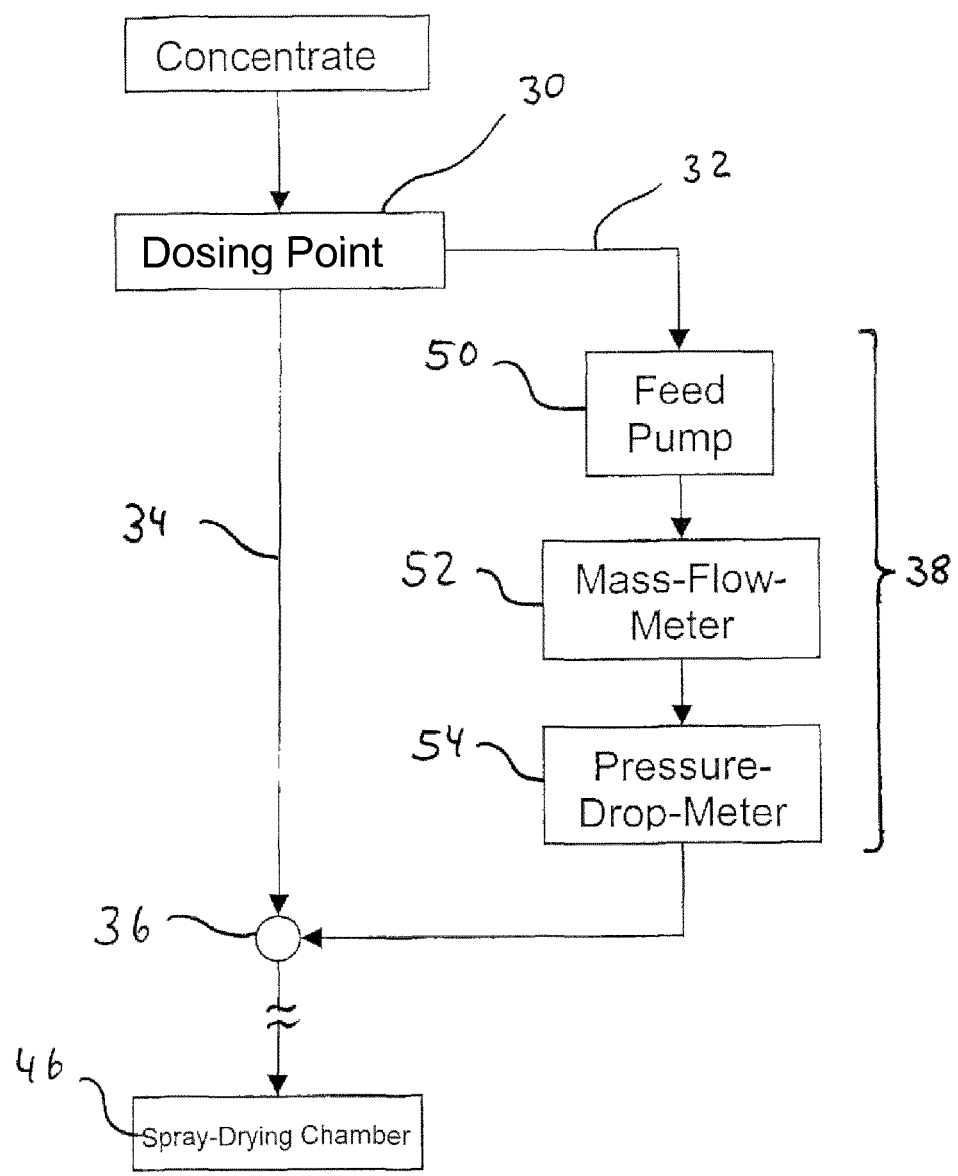
FIG. 7 is a flow chart of the differential pressure drop method.

The inner thread 15 of the adjusting pin 13 serves to be brought into a threaded engagement with an outer thread 16 of a plunger 17 more clearly shown in FIGS. 5 and 5A.

Figure 4:
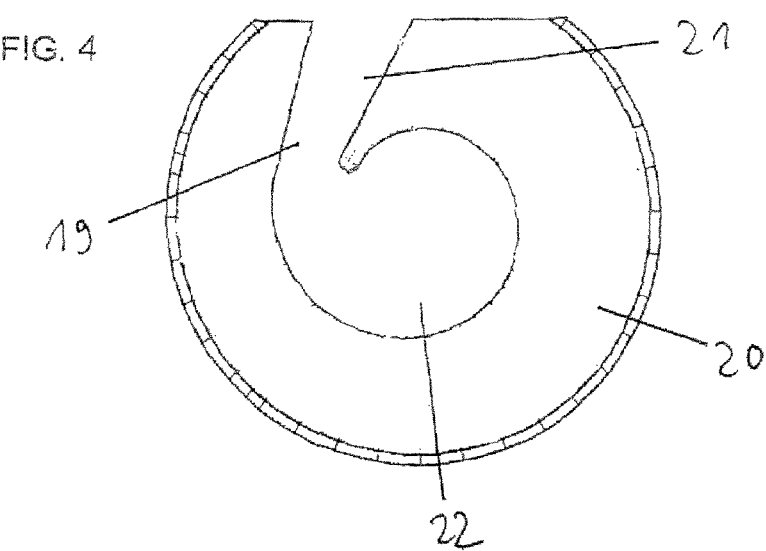
FIG. 4 shows a front view of the swirl chamber body of the spray nozzle apparatus of FIG. 1.

As can be seen from FIGS. 5 and 5A, the plunger 17 comprises an outer circumferential surface section 18 with a helicoidally shaped cross section corresponding to the shape and size of a receiving section 19 of a swirl chamber body 20 accommodated in a nozzle body 23 which is mounted to the connecting sleeve 9 as shown in FIG. 4.

The swirl chamber body 20 comprises a lateral or tangential inlet channel 21 for introducing paste material or the like into the swirl chamber 22 of the swirl chamber body 20.

Material to be transported through the inlet channel 21 into the swirl chamber 22 can enter the nozzle body 23 via a first orifice 24 or inlet orifice which extends radially to the common longitudinal axis 28 of the nozzle body 23 and the connecting sleeve 9. To this end there is a tube 25 connected to the first orifice 24 of the nozzle body 23 defining an inlet opening of the apparatus 1.

Paste or paste like material delivered to the nozzle body 23 via the tube 25 enters the nozzle body 23 via the first orifice 24 and enters the swirl chamber 22 via the inlet channel 21.

The swirl chamber 22 is equipped with an axially extending through hole having an inner circumferential surface section with a helicoidally shaped cross section, thus forming a helicoidal, spiral-type guiding face that serves to accelerate the material into the direction of a second orifice 26 or nozzle orifice of the nozzle body 23 defining an outlet opening of the apparatus 1. An orifice plate 27 is provided between the axial outlet of the swirl chamber 22 and the second orifice 26 by which orifice plate 27 the opening angle of the spray cone can be basically adjusted.

FIG. 1 shows the plunger 17 closing the first orifice 24. Driving the motor 4 makes the hollow shaft 7 rotate and thus also makes the adjusting pin 13 rotate about its longitudinal axis. The plunger 17 is connected to the inner thread 15 of the adjusting pin 13 via the outer thread 16 and can only execute a movement relative to the swirl chamber body 20 along the longitudinal axis 28 of the plunger 17 but can not rotate relative to the swirl chamber body 20. Thus a rotation of the adjusting pin 13 is transformed in to an axial movement of the plunger 19 relative to the swirl chamber body 20.

By this movement of the plunger 18 the axial width of the first orifice 24 and the geometry of the swirl chamber 22 and thus the nozzle chamber can be modified. Since the electric drive 2 is controlled by process and product parameters which in turn are obtained or evaluated inline during the manufacturing process of the powder to be achieved, the control takes place inline with the manufacturing process of the powder. To achieve this, the control circuit provides the electric drive 2 with signals such that the plunger 17 is being moved axially in the direction of the longitudinal axis 28 as shown in FIG. 1. By this movement of the plunger 17 the spray droplet size of the sprayed material to be atomized can be adjusted towards the minimum Sauter diameter possible for a given set of input parameters.

Measuring these input parameters inline with the production process of the powder according to the method of the invention allows adjusting of the droplet size towards the minimum Sauter diameter possible inline and thus makes it possible to consider the complete range of spray viscosities during the production process of the powder to be produced.

The product paste entering the swirl chamber through the inlet channel 21 follows a helicoidal and spiral way due to the spiral-type cross section design of the swirl chamber in a combined circumferential and axial direction towards the nozzle orifice 26. This design accelerates the traveling speed of the product paste flow in the swirl chamber, provided that the mass flow of the product paste is constant. The product paste is leaving the spray nozzle through the orifice plate 27 and the nozzle orifice 26 as a cone-shaped film 29 with a cone tip angle α wherein the film 29 atomizes into droplets forming a spray mist. The cone tip angle α is directly proportional to the traveling speed of the product paste in the nozzle orifice 26, i.e. the higher the traveling speed is, the larger the cone tip angle becomes and the smaller the droplets size.

A cone tip angle α of 0° generates no atomization and, in a realized example, a cone tip angle α of 100° generates droplets having a Sauter-diameter of $D_{32}$=30 μm. The wider the cone tip angle α is, the smaller the droplets become so that the droplet size can be controlled by the cone tip angle α and thus by the traveling speed of the product paste in the nozzle orifice 26

FIG. 6 is a flowchart of the process control method according to the present invention. The product paste in FIG. 6 indicated as "concentrate" is delivered to a dosing point 30, which leads a part of the product paste stream into a bypass line 32. The majority of the product paste stream is directed into a main product paste line 34. The bypass line 32 is redirected into the main product paste line 34 at a line junction 36 downstream of a differential pressure drop measuring apparatus 38 provided in the bypass line 32.

Downstream of the line junction 36 a mass flow meter 40, a density meter 42 and a spray pressure probe 44 are provided in the main product paste line. Downstream of the spray pressure probe 44 the main product paste line 34 enters the spray nozzle apparatus 1 shown in FIG. 1 through tube 25. The product paste delivered to the spray nozzle apparatus 1 is then sprayed into a spray drying chamber 46.

The differential pressure drop measuring apparatus 38 determines the shear rate and the shear viscosity η of the product paste delivered to the spray nozzle. The data of the shear rate and shear viscosity η are delivered from the differential pressure drop measuring apparatus 38 to a control device (SPS-control) 48. In the same manner, the product paste mass flow rate $Q_m$ determined in the mass flow meter 40, the product paste density ρ determined in the density meter 42 and the spray pressure P of the product paste determined in the spray pressure probe 44 are also delivered to the control device 48.

Control device 48 comprises a computer which calculates an output control parameter based on the above data delivered to the control device 48 and on the basis of known spray nozzle geometry parameters stored in a memory of the control device 48. The output control parameter is delivered to the spray nozzle apparatus 1 in order to adjust the swirl chamber piston 17 to a calculated position in order to obtain a desired swirl chamber volume.

The following equations 1-7 describe the solving procedure how to control the plunger position (given with $h_{sc}$) based on a change in the paste shear viscosity η.

Accordingly the solving procedure is applied for a change in mass flow rate Qm and paste density ρ.

Universal Massflow-Characterisation of Pressure Swirl Nozzle Flows:

$$\frac{Qm}{\eta d_{sc}} = 2.1844\left(\frac{d_{or}}{d_{sc}}\right)^{1.2859}\left(\frac{h_{sc}}{d_{sc}}\right)^{0.4611}\left(\frac{\sqrt{P\rho}\,d_{sc}}{\eta}\right)^{0.9140} \tag{1}$$

The relation between spray pressure P and axial position of the plunger (given with $h_{sc}$) is derived for the example of a shear viscosity change from $\eta_{old}$ to $\eta_{new}$:

$$\frac{\eta_{new}}{\eta_{old}} = \left(\frac{h_{sc,old}}{h_{sc,new}}\right)^{0.4611}\left(\frac{\eta_{new}}{\eta_{old}}\right)^{0.9140}\left(\frac{P_{old}}{P_{new}}\right)^{\frac{0.9140}{2}} \tag{2}$$

Solved for the spray pressure ratio:

$$\frac{P_{old}}{P_{new}} = \left(\frac{\eta_{new}}{\eta_{old}}\right)^{\frac{1-0.9140}{0.4570}}\left(\frac{h_{sc,old}}{h_{sc,new}}\right)^{\frac{-0.4611}{0.4570}} \tag{3}$$

In order to find a direct relation between plunger position $h_{sc}$ and shear viscosity η, the spray pressure ratio has to be found from another equation, see equations 4-6 below: Universal Spray Droplet Size Characterisation of Pressure Swirl Nozzle Sprays:

$$\frac{D_{32,global}}{d_{sc}} = 1.0798\ Re^{-0.2987}We^{-0.1709}\left(\frac{h_{sc}}{d_{sc}}\right)^{-0.0772}\left(\frac{d_{or}}{d_{sc}}\right)^{0.9534} \tag{4}$$

Again, one can derive the Spray Pressure Ratio with the consistency conditions that $D_{32\text{-}global\text{-}old}$ and $D_{32\text{-}global\text{-}new}$ remain constant:

$$\frac{D_{32,global,old}}{D_{32,global,new}} = \tag{5}$$

$$1 = \left(\frac{Re_{old}}{Re_{new}}\right)^{-0.2987}\left(\frac{We_{old}}{We_{new}}\right)^{-0.1709}\left(\frac{h_{sc,old}}{h_{sc,new}}\right)^{-0.0772} = \left(\frac{h_{sc,old}}{h_{sc,new}}\right)^{-0.2987}$$

$$\left(\frac{\eta_{old}}{\eta_{new}}\right)^{0.2987}\left(\frac{h_{sc,old}}{h_{sc,new}}\right)^{0.2987}\left(\frac{h_{sc,old}}{h_{sc,new}}\right)^{0.1709\cdot 2}\left(\frac{h_{sc,old}}{h_{sc,new}}\right)^{-0.0772}$$

And hence the solution, how to control the plunger height $h_{sc,new}$ based on a current position $h_{sc,old}$:

$$\frac{h_{sc,new}}{h_{sc,old}} = \left(\frac{\eta_{new}}{\eta_{old}}\right)^{-1.1289} \tag{6}$$

Combining equations 3 and 6 one receives the solution, how to control the spray pressure:

$$\frac{P_{new}}{P_{old}} = \left(\frac{\eta_{new}}{\eta_{old}}\right)^{0.9508} \tag{7}$$

FIG. 7 is a flowchart of the differential pressure drop method as applied in the differential pressure drop measuring apparatus 38. A feed pump 50 is provided in the bypass line 32 downstream of dosing point 30. The feed pump 50 ensures a constant feed-flow-rate in the differential pressure drop measuring apparatus 38 to enable shear rates which cover the second Newtonian viscosity plateau. Downstream of the feed pump 50 a mass flow meter 52 is provided through which the product paste in the bypass line 32 is directed into a pressure drop meter 54. The shear viscosity (η) of the product paste in the bypass line 32 is calculated from the mass flow measured in the mass flow meter 52, the known product density of the product paste and the pressure drop measured in the pressure drop meter 54. This calculation is either made in a computer (not shown) of the differential pressure drop measuring apparatus 38 or, the respective data are delivered to the control device 48 and the shear viscosity η is calculated in the computer of the control device 48. In order to consider the fact that the pressure drop is measured in a bypass line 32 the bypass mass flowrate is adjusted by the feed pump 50 until the shear-rate is such, that the second Newtonian plateau viscosity can be measured by the pressure drop-meter 54 within laminar flow conditions.

In the present example the dosing point 30 regulates the bypass flow rate to keep the bypass flow pressure <20 bar at laminar flow conditions, e.g. flow rates <1000 kg/h.

Figure 8:
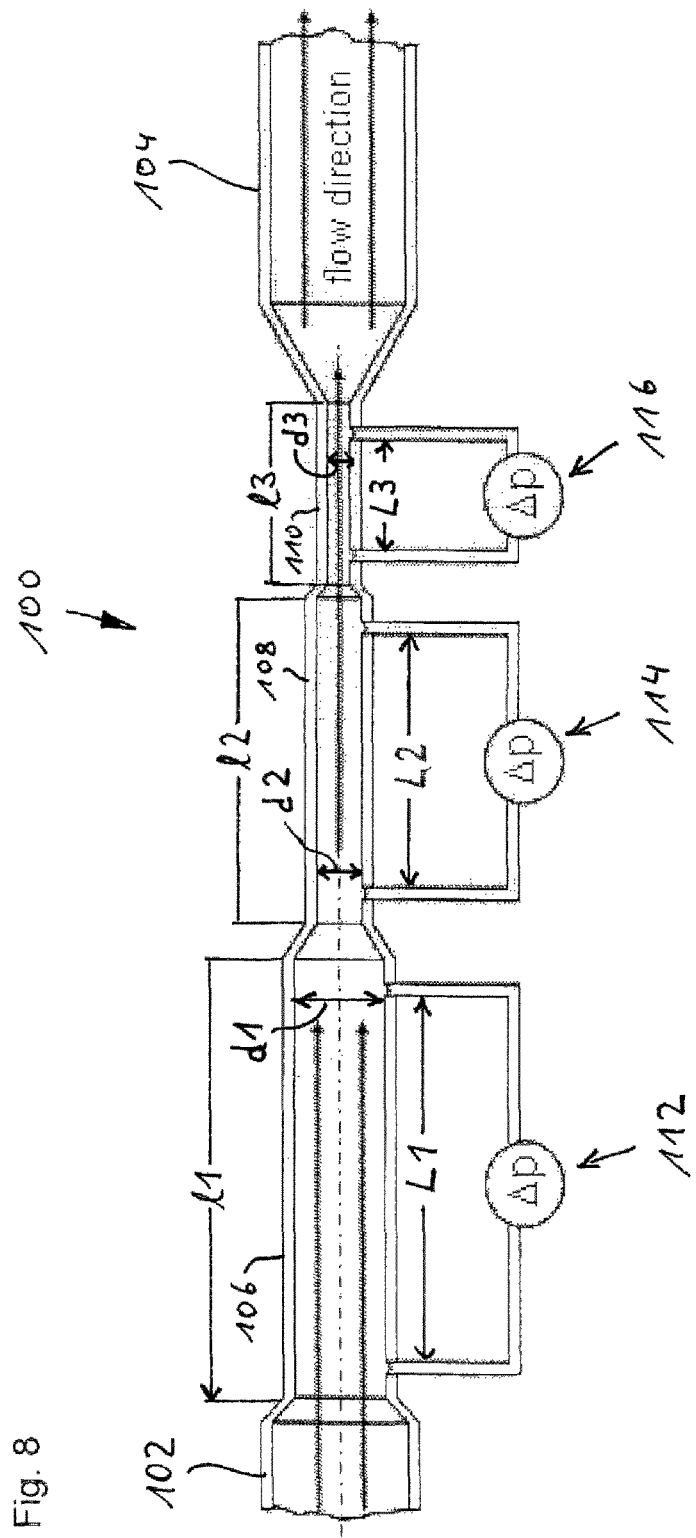
FIG. 8 shows a principle of a measuring apparatus for the differential pressure drop method and FIG. 9 shows an example of a dimensionless correlation between the droplet size of the spray and the geometry, process and product parameters.

FIG. 8 shows the principle of a measuring apparatus (pressure drop meter) for the differential pressure drop method for determination of the second Newtonian plateau viscosity using three independent pressure drop recordings at three different shear-rates.

The pressure drop meter 100 comprises a tube having a fluid inlet section 102 and a fluid outlet section 104 and three pressure drop measuring sections 106, 108, 110 provided between the inlet section 102 and the outlet section 104. The first pressure drop measuring section 106 which is close to the inlet section 102 has a first internal diameter $d_1$ and a first axial length $l_1$. A first differential pressure meter 112 measuring a first pressure drop $\Delta p_1$ is connected to the first pressure drop measuring section 106 in a commonly known matter wherein the axial distance $L_1$ between the two static pressure measuring openings in the wall of the first pressure drop measuring section 106 is substantially equal to the length $l_1$ of the first pressure drop measuring section 106.

The second pressure drop measuring section 108 is provided downstream of the first pressure drop measuring section 106. The internal diameter $d_2$ of the second pressure drop measuring section 108 is smaller than the diameter $d_1$ of the first pressure drop measuring section. The length $l_2$ of the second pressure drop measuring section 108 is shorter than the length of the first pressure drop measuring section 106. The second pressure drop measuring section 108 comprises a second differential pressure meter 114 measuring a second pressure drop $\Delta p_2$ wherein the distance $L_2$ between the two static pressure measuring openings in the wall of the second pressure drop measuring section 108 is shorter than the distance $L_1$ of the first differential pressure meter 112.

A third pressure drop measuring section 110 is provided downstream of the second pressure drop measuring section 108 and the third pressure drop measuring section 110 opens into the outlet section 104. The internal diameter $d_3$ of the third pressure drop measuring section 110 is smaller than the diameter $d_2$ of the second pressure drop measuring section 108 and the length $l_3$ of the third pressure drop measuring section is shorter than the length $l_2$ of the second pressure drop measuring section. The third pressure drop measuring section 110 comprises in a commonly known manner a third differential pressure meter 116 measuring a third pressure drop $\Delta p_3$. The distance $L_3$ between the two static pressure measuring openings in the wall of the third pressure drop measuring section 110 is shorter than the distance $L_2$ of the second differential pressure meter 114.

The differential pressure drop meter 100 allows the measurement of three independent pressure drop recordings of the first, the second and the third differential pressure drop meters. Utilizing these three differential pressure drop probes in series, a single mass flow rate causes three increasing wall shear rates with the decreasing tube diameter.

The following equation 8 is used to calculate the shear viscosity η for laminar tube flows (Re<2300), applied to all 3 differential pressures $\Delta p_1$, $\Delta p_2$ and $\Delta p_3$ (respectively measured at 112, 114 and 116, FIG. 8), by replacing $\Delta p_i$ and the corresponding tube dimensions ($R_i$ and $L_i$) in equation 8:

Only, if the shear viscosity $\eta_i$ is equal ($\eta_1 = \eta_2 = \eta_3$) between the 3 differential pressures, the $2^{nd}$ Newtonian shear viscosity is found and used e.g. in equation 1 and 7. etc. . . .

$$\eta_i = \frac{\pi \cdot R_i^4 \cdot \Delta p_i \cdot \rho}{8 \cdot Qm \cdot L_i} \quad (8)$$

with following definitions of symbols:
$R_i$: tube radius ($R_1$, $R_2$ and $R_3$) in [m]
$\Delta p_i$: tube pressure drop ($\Delta p_1$, $\Delta p_2$ and $\Delta p_3$) in [Pa]
$\rho$: product density in [kg/m3]
Qm: mass flow rate in [kg/s]
$L_i$: tube length (distance $L_1$, $L_2$ and $L_3$) in [m]

Figure 9:
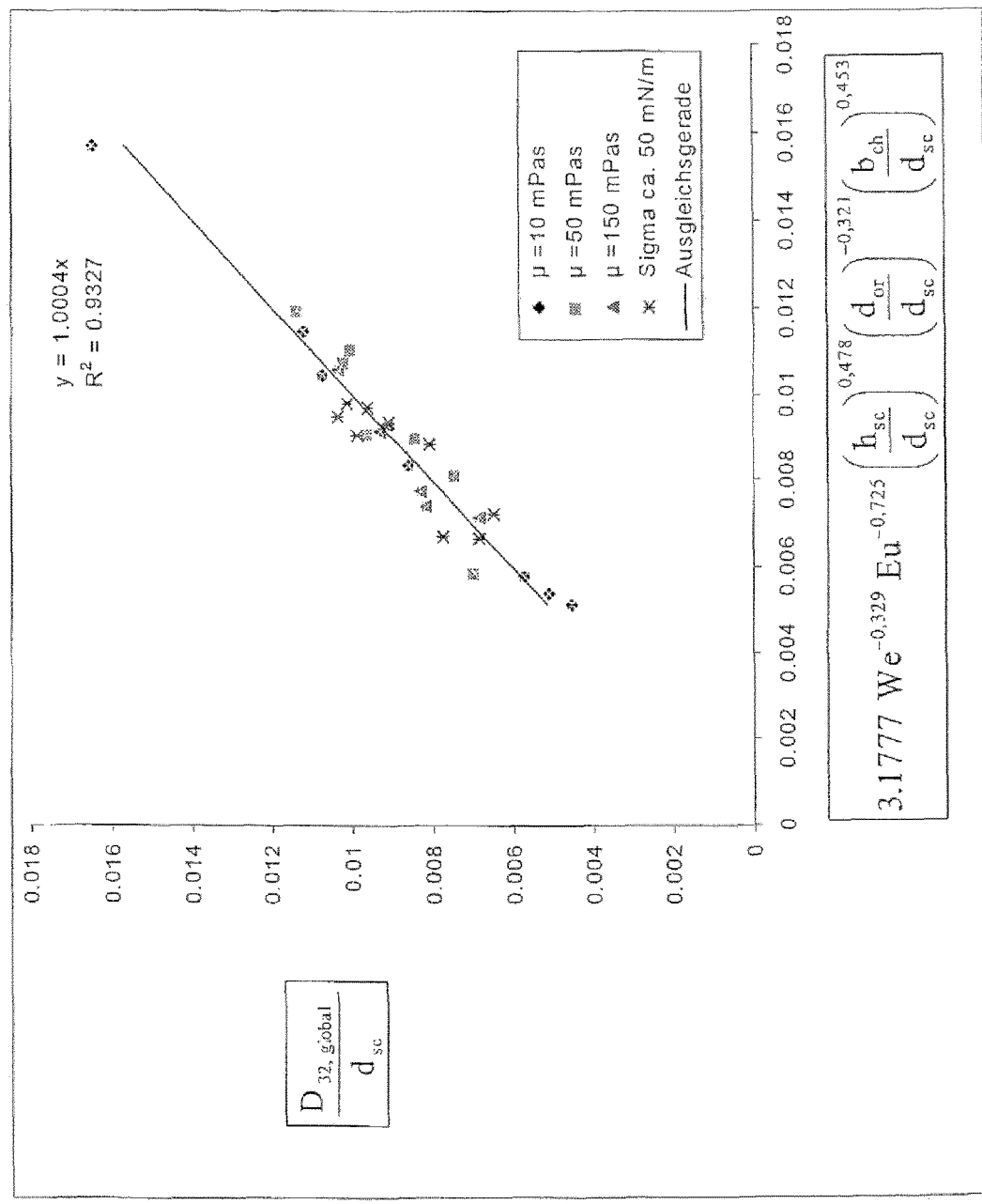

FIG. 9 shows an example of a dimensionless correlation between the droplet size of the spray and the geometry, process and product parameters. The droplet size $D_{32,\,global}$ is the Sauter diameter of the spray droplets. The dimensionless Weber number We and the Euler number Eu represent the four input process parameters: Spray mass flow rate $Q_m$, static spray pressure P, product density ρ and product shear viscosity η. The geometry of the spray nozzle is described with the parameters $h_{sc}$, $d_{sc}$, $d_{or}$ and $b_{ch}$. These abbreviations are explained in table 1 below.

The Sauter diameter $D_{32,\,global}$ was measured by phase-doppler anemometry (PDA) of the droplets sprayed by the spray nozzle apparatus.

The measured Sauter diameter $D_{32,\,global}$ was correlated to the corresponding geometry, process and product parameters, which were varied in the frame of the PDA measurements to achieve a correlation as shown in FIG. 9.

TABLE 1

Abbreviations and formula

| Symbol, Abbreviation | Description | Units |
|---|---|---|
| $D_{32,global}$ | Global Sauter diameter as found from PDA measurements of spray | [m] |
| $d_{sc}$ | Swirl chanber diameter (smallest diameter of swirl chanber spiral) | [m] |
| $h_{sc}$ | Swirl chamber height (axial height of swirl chamber) | [m] |
| $d_{or}$ | Orifice diameter (diameter of opening made in orifice plate) | [m] |
| $b_{ch}$ | Width of swirl chamber inlet channel (smallest width of inlet channel which leads into the swirl chamber) | [m] |
| We | Weber number $$We = \frac{\rho_{liquid} u_{bulk}^2 d_{orifice}}{\sigma_{liquid}}$$ | — |
| Eu | Euler number $$Eu = \frac{P}{\rho_{liquid} u_{bulk}^2}$$ | — |
| Re | Reynolds number $$Re = \frac{\rho_{liquid} u_{bulk} h_{sc}}{\mu}$$ | — |

TABLE 1-continued

Abbreviations and formula

| Symbol, Abbreviation | Description | Units |
|---|---|---|
| $u_{bulk}$ | Bulk velocity at swirl chamber inlet | [m/s] |
| $u_{bulk} = \dfrac{Qm}{\rho_{liquid} h_{sc} b_{ch}}$ | | |
| Qm | Mass flow rate | [kg/s] |
| P | Spray pressure | [Pa] |
| $\rho_{liquid}$ | Liquid density | [kg/m³] |
| $\eta_{liquid}$ | Liquid chear viscosity | [Pas] |
| $\sigma_{liquid}$ | Surface tension | [N/m] |
| PDA | Phase-Doppler Anemometry | — |

The invention should not be regarded as being limited to the embodiment shown and described in the above but various modifications and combinations of features may be carried out without departing from the scope of the following claims.

The invention claimed is:

1. A method of controlling a spray droplet size of a spray nozzle apparatus comprising a spray nozzle, the method comprises the following steps of:
   a) providing a paste of a product to be sprayed by the spray nozzle;
   b) continuously determining a shear viscosity of the product paste delivered to the spray nozzle;
   c) determining a mass flow rate of the product paste delivered to the spray nozzle;
   d) determining a static pressure of the product paste delivered to the spray nozzle;
   e) determining a density of the product paste delivered to the spray nozzle;
   f) delivering data obtained in steps b) to e) to a control device comprising a computer and a memory;
   g) calculating control data for adjusting the spray nozzle on the basis of the data obtained in steps b) to e) and on nozzle geometry parameters stored in the memory; and
   h) sending the control data as control signals to a control means of the spray nozzle and adjusting the spray nozzle accordingly.

2. The method according to claim 1, wherein the step b) of continuously determining the shear viscosity of the product paste delivered to the spray nozzle is carried out in a bypass to a product paste stream to the spray nozzle.

3. The method according to claim 1, wherein the shear viscosity of the product paste is determined by the following steps:
   b1) providing a constant feed-flow-rate of the product paste;
   b2) determining the mass flow rate of the product paste;
   b3) delivering the product paste to a pressure-drop-meter and determining a pressure drop; and
   b4) calculating a shear rate and shear viscosity of the product paste on the basis of the mass flow determined in step b2), the pressure drop determined in step b3) and a known product density.

4. The method according to claim 3, wherein the calculation in step b4) considers also a bypass-mass-flow-rate.

5. The method according to claim 3, wherein the determination of the pressure drop in step b3) is carried out according to a differential pressure drop method.

6. The method according to claim 5, wherein the adjusting of the spray nozzle in step h) is carried out by changing a volume of a swirl chamber provided in the spray nozzle.

7. A spray drying apparatus comprising:
   a spray nozzle provided with a nozzle orifice for outputting spray droplets of a product to be dried and an inlet orifice for transferring the product into a nozzle chamber;
   an adjustment apparatus configured for adjusting the size of the outputted droplets inline during the spray process on the basis of control data calculated by determining a shear viscosity and a mass flow rate of product delivered to the spray nozzle, the adjustment apparatus comprises a member for adjusting a nozzle chamber geometry based on spray drying process parameters and product parameters obtained inline during the spray drying process; wherein the member for adjusting the nozzle chamber geometry comprises an electric drive and a connecting sleeve,
   the electric drive adjusting the nozzle chamber geometry, the electric drive controlled by a control device based on the spray drying process parameters and the product parameters; and
   the connecting sleeve releasably fixed to the electric drive and providing a longitudinal bore for rotatingly accommodating a hollow shaft which transfers a rotating motion of an output shaft of the electric drive to an adjusting pin driving a plunger into and out of the nozzle chamber, the plunger is axially movable, and the adjusting pin is provided with a longitudinally extending axial bore with an inner thread in engagement with an outer thread of the plunger such that a rotating motion of the adjusting pin is transferred to a longitudinal motion of the plunger.

8. The spray drying apparatus according to claim 7, wherein the plunger is configured for adjusting a size of the inlet orifice and/or a volume of the nozzle chamber.

9. The spray drying apparatus according to claim 8, wherein the plunger is movable into and out of the nozzle chamber by the electric drive adjusting a width and/or a height of the inlet orifice of the nozzle chamber.

10. The spray drying apparatus according to claim 8, wherein the electric drive comprises an electric motor configured for rotatingly driving the output shaft, the rotation of the output shaft being transferred to the longitudinal motion of the plunger via a threaded engagement between the output shaft and the plunger.

11. The spray drying apparatus according to claim 7, wherein the nozzle chamber is provided by a swirl chamber body inserted into an inner chamber of a nozzle body, the nozzle body releasably fixed to the connecting sleeve, and the swirl chamber body provided with an opening channel which is arranged in correspondence to the inlet orifice for entering the product into a swirl chamber of the swirl chamber body.

12. The spray drying apparatus according to claim 11, wherein the swirl chamber is provided with a helicoidally tightening guiding face configured for accelerating the product into the direction of the nozzle orifice.

13. The spray drying apparatus according to claim 7, wherein the inlet orifice extends radially to a longitudinal axis of the nozzle, and the product is transferred to the nozzle via a tubing connected with the inlet orifice.

14. The spray drying apparatus according to claim 7, wherein the nozzle orifice is equipped with a releasably mounted orifice plate such that an opening diameter of the nozzle orifice is configured to be variable by replacing the orifice plate by a different diameter orifice plate.

15. The spray drying apparatus according to claim 8, in which (i) a cone angle of a spray mist produced by product droplets and (ii) a droplet size are both variable by axially moving the plunger relative to the nozzle chamber.

* * * * *